(12) United States Patent
Polliack et al.

(10) Patent No.: US 8,192,383 B2
(45) Date of Patent: Jun. 5, 2012

(54) EMERGENCY STABILIZATION OF A FRACTURED PELVIS

(75) Inventors: Adrian Abram Polliack, Lake Oswego, OR (US); Lance David Hopman, Tigard, OR (US)

(73) Assignee: The Seaberg Company, Inc., Wilsonville, OR (US)

( * ) Notice: Subject to any disclaimer, the term of this patent is extended or adjusted under 35 U.S.C. 154(b) by 481 days.

(21) Appl. No.: 12/462,754

(22) Filed: Aug. 7, 2009

(65) Prior Publication Data
US 2011/0034845 A1 Feb. 10, 2011

(51) Int. Cl.
*A61F 5/00* (2006.01)
*A61F 5/24* (2006.01)
*A41F 9/00* (2006.01)

(52) U.S. Cl. .............................. 602/19; 128/96.1; 2/311
(58) Field of Classification Search ............... 602/19, 602/36, 5, 23–24, 32, 38–39, 60, 67–68; 128/96.1, 98.1, 99.1, 100.1, 101.1, 869, 876; 2/311–324, 309; 24/68 R, 585, 31 R, 32, 24/33, 36, 578.15, 579.09; 601/71, 124
See application file for complete search history.

(56) References Cited

U.S. PATENT DOCUMENTS

| | | | | |
|---|---|---|---|---|
| 2,554,337 A | * | 5/1951 | Lampert | 606/237 |
| 3,594,872 A | | 7/1971 | Kulwin et al. | |
| 4,390,014 A | | 6/1983 | Forman | |
| 4,459,979 A | | 7/1984 | Lewis, Jr. | |
| 4,545,370 A | * | 10/1985 | Welsh | 602/19 |
| 4,715,364 A | * | 12/1987 | Noguchi | 128/96.1 |
| 4,964,401 A | | 10/1990 | Taigen | |
| 4,991,573 A | | 2/1991 | Miller | |
| 5,086,759 A | | 2/1992 | Buddingh | |
| 5,307,521 A | | 5/1994 | Davis | |
| 5,407,422 A | | 4/1995 | Matthijs et al. | |
| 5,489,260 A | | 2/1996 | Striano | |
| 5,500,959 A | * | 3/1996 | Yewer, Jr. | 602/19 |
| 5,551,085 A | | 9/1996 | Leighton | |
| 5,695,453 A | | 12/1997 | Neal | |
| 5,785,671 A | | 7/1998 | Striano | |
| 6,053,883 A | | 4/2000 | Schiek, Sr. | |
| 6,165,147 A | | 12/2000 | Morrow | |
| 6,240,923 B1 | | 6/2001 | Barrick | |

(Continued)

FOREIGN PATENT DOCUMENTS

| | | |
|---|---|---|
| KR | 900005852 B1 | 8/1990 |
| WO | 0045756 A1 | 8/2000 |
| WO | WO 00/45756 | 8/2000 |
| WO | 0189433 A1 | 11/2001 |
| WO | 03005743 A2 | 9/2003 |
| WO | 2011016824 A3 | 2/2011 |

OTHER PUBLICATIONS

International Search Report, PCT/US2010/001682, Feb. 10, 2011, The Seaberg Company, 5 pages. International Preliminary Report on Patentability and Written Opinion, PCT/US2010/001682, Feb. 7, 2012, The Seaberg Company, 5 pages.

*Primary Examiner* — Patricia Bianco
*Assistant Examiner* — Tarla Patel
(74) *Attorney, Agent, or Firm* — Chernoff Vilhauer LLP (57) ABSTRACT

A hip-girdling pelvic sling device for maintaining a desired amount of tension surrounding a person's hips and pelvis to securely support and stabilize a pelvis that has been fractured. Areas of mating types of fastener material such as mating hook-bearing fastener material and loop pile fastener material are arranged on the device to enable a strap to be secured at various effective lengths to provide a wide range of adjustability to make the device useful for persons of various sizes.

12 Claims, 6 Drawing Sheets

U.S. PATENT DOCUMENTS

| | | |
|---|---|---|
| 6,352,074 B1 | 3/2002 | Okada |
| 6,503,217 B1 | 1/2003 | Gibbs et al. |
| 6,554,784 B1 | 4/2003 | Krieg et al. |
| 6,610,022 B1 | 8/2003 | Ashbaugh et al. |
| 7,008,389 B2 | 3/2006 | Krieg et al. |
| 7,094,213 B1 | 8/2006 | Cook |
| 2001/0053884 A1 | 12/2001 | Krieg et al. |
| 2005/0283102 A1 | 12/2005 | Schwenn et al. |
| 2006/0135898 A1 | 6/2006 | Richardson |
| 2006/0206992 A1* | 9/2006 | Godshaw et al. ............... 2/338 |
| 2008/0251087 A1 | 10/2008 | Richardson |

* cited by examiner

EMERGENCY STABILIZATION OF A FRACTURED PELVIS

BACKGROUND OF THE INVENTION

The present invention relates to emergency treatment of a fractured pelvis. In particular, the invention provides a device and a method for its use in a closed reduction of a fracture of a pelvis and for stabilizing the fractured pelvis pending further treatment.

Internal bleeding due to a fractured pelvis can easily result in death. Rapidly reducing a fracture of a pelvis decreases mortality substantially, and devices are known for reducing a fracture and stabilizing the fractured pelvis in emergency situations, so that a patient can be transported to a hospital or other treatment facility. Stabilization of the pelvis within the first hour after a fracture occurs is critical and may often determine whether the patient lives or dies.

Krieg, et al., U.S. Pat. Nos. 6,554,784 and 7,008,389 disclose devices which can be used to encircle the hips of an injured person and provide a proper amount of hoop tension to urge the parts of a person's fractured pelvic ring toward a normal relationship and thus reduce internal bleeding at the site or sites of fracture. The devices disclosed by Krieg, et al., provide for non-invasive reduction of a fractured pelvis and for stabilization of the person's pelvis during transport to a hospital or other medical facility where a fractured pelvis can be surgically repaired. The Krieg, et al., devices are particularly appropriate for use in emergency situations such as the scene of a car accident, a skiing accident, a mountain-climbing accident, or industrial injury, for example.

In a commercially available embodiment of a Krieg, et al., device, a broad belt-like body partially encircles the patient's hip region, and a strap adjustably interconnects the opposite ends of the body of the device. A special buckle is attached to one end of the body of the device, and a strap extends between the buckle and a strap mounting piece that must be fastened to the opposite end of the main body at a location that must be selected when using the device on an injured person, although proper placement of the strap mounting piece is not intuitively obvious to an untrained person. The strap, extending through the buckle, must then be pulled to provide hoop tension to support the pelvis. The special buckle senses the correct amount of tension, at which it engages the strap, preventing over tightening. A relatively small range of adjustability of the circumference of the device is available, however, with the strap mounting piece in a particular location. As a result the strap mounting piece may need to be relocated on the main body before sufficient tension can be obtained and retained by the buckle.

Because of the provision of the strap and its mounting piece as a separate, removable, part of the device, application of the device involves several steps, so proper training and familiarity with the device can be critical to its effective use. Also, the removability of the strap requires a well-trained person to rearrange the parts of the device properly for reuse once it has been used on an injured person.

In order to avoid the expenditure of time required to determine where to attach the strap mounting piece to the main body of such a device, and to simplify effective application, an improved pelvis stabilizing device is desired, in which such placement of a strap mounting member onto the main body of the device is not necessary, yet ample adjustability is immediately available.

SUMMARY OF THE INVENTION

The present invention, as defined by the claims which form a part of the disclosure herein, provides an answer to the aforementioned need for a simplified device for encircling a pelvis that has been fractured, reducing the fracture, and stabilizing the pelvis by providing a proper amount of encircling tension.

As a first aspect of a device as disclosed herein, a belt-like main body of a device for stabilizing a fractured pelvis has a pair of opposite end portions, one of which carries a buckle, and the other of which has an inner end of a strap member attached thereto. The strap member is arranged to extend through the buckle and to be doubled back to extend toward the end of the main body to which its inner end is attached. Fastener material is present in locations providing a wide range of adjustment of the effective length of the strap connection between the end of the body of the device and the buckle through which the strap extends.

In one embodiment of the device disclosed herein, fastening material such as Velcro™ hook-bearing fastener material is provided on an outer end portion of the strap, and material such as Velcro™ loop-bearing fastener material is provided along an intermediate portion of the strap.

In one embodiment of the device, a surface of the main body of the device at the end from which the strap extends is securely and matingly receptive to hook-bearing fastener material such as Velcro™ hook-bearing fastener material located on the outer end portion of the strap.

In one embodiment of the device disclosed herein, material of much of the outer face of the end portion of the main body of the device is receptive to fastener material of the Velcro™ hook-bearing type, and an area of hook-bearing fastener material of the Velcro™ type is located where it can engage and grip the loop-bearing fastener material on the intermediate portion of the strap when the strap is doubled back alongside itself and pulled through the buckle far enough for the device to fit around the pelvic area of a relatively slender injured person with the necessary amount of tension.

The foregoing and other features of the invention will be more readily understood upon consideration of the following detailed description of the invention taken in conjunction with the accompanying drawings.

DETAILED DESCRIPTION OF EMBODIMENTS

Figure 1:
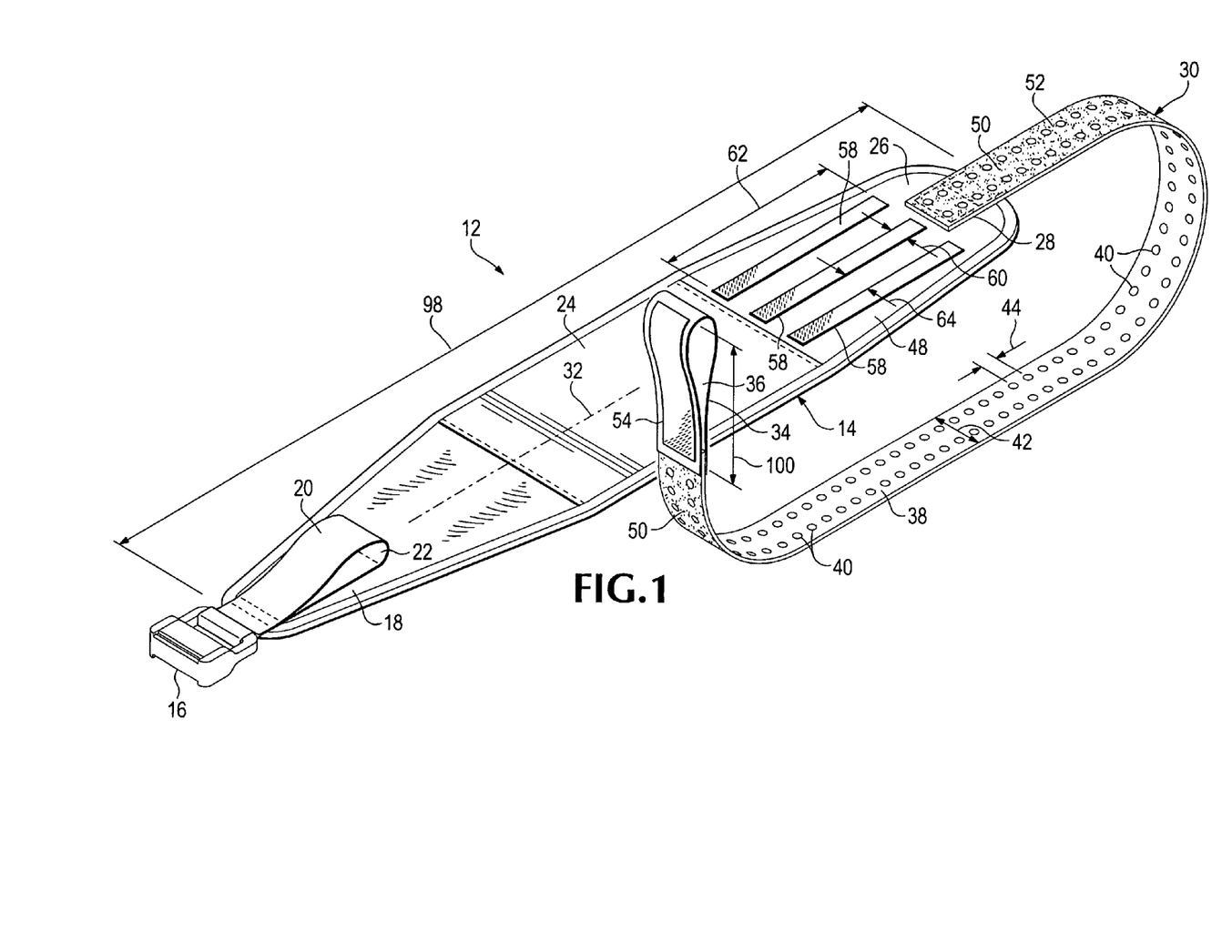
FIG. 1 is an isometric view of a pelvis-stabilizing device that is an exemplary embodiment of an aspect of the present invention.

Referring first to FIGS. 1-4 of the drawings which form a part of the disclosure herein, a pelvis supporting and stabilizing device 12 for stabilizing a fractured pelvis, hereinafter often called a pelvic sling, is shown in FIG. 1 ready for application to a person to provide stabilization and support for a fractured pelvic ring by encircling the hip region of a person. A main body portion 14 is of strong flexible material and has the general shape of a wide belt. A buckle 16 is attached to a first end portion 18 of the main body 14 by a small loop of a strap 20 of strong fabric such as woven webbing, permanently attached to the first end portion 18, as by being sewn securely to it. As used herein the term "permanently attached" means that removal and reattachment are not easily accomplished by a user and cannot be accomplished readily without use of equipment such as that needed for initial manufacture. The fabric of the strap 20 also defines a large loop 22, attached to the first end portion 18 so that it can be used as a handle by a person applying the pelvic sling 12 to an injured person, as will be explained more fully presently.

A central portion of the main body 14 may be covered on an exterior face by a sheet 24 of low friction flexible plastic material which will be exposed on the posterior side of a person on whom the pelvic sling 12 is in use, facilitating movement of such person on a backboard or other support.

At a second end portion 26, opposite the first end portion 18, an inner end 28 of an elongate flexible strap 30 is permanently attached to the main body 14, as by being sewn, riveted, or thermally or sonically welded securely to the second end portion 26 of the main body 14. The strap 30 extends longitudinally away from the second end portion 26, generally aligned with the longitudinal axis 32 of the main body 14. An outer end portion 34 of the strap 30 may include a loop 36 of strong fabric such as Nylon webbing attached to an intermediate portion 38 of the strap 30, which may be of heavier and consequently slightly stiffer, yet still flexible, webbing. The loop 36 may be securely sewn or otherwise permanently attached to the intermediate portion 38 of the strap 30. The loop 36 is thus available for use as a handle to pull the strap 30 away from the buckle 16, as will be explained more fully presently.

Pairs of holes 40 may be defined in the intermediate portion 38 of the strap 30. The holes 40 of each pair are aligned with each other transversely across the width 42 of the strap 30 and loop 36, which may be about two inches, for example. Adjacent pairs of holes 40 may be evenly spaced apart longitudinally of the strap 30 at a pitch 44 of, for example, 0.625 inch, so as to permit the effective circumference of the pelvic sling 12 to be adjusted in increments small enough to provide a desirable amount of tension in the pelvic sling 12 encircling a person's hips to stabilize a fractured pelvis.

The main body portion 14 may be of laminated fabric, and may include a central layer of padding material (not shown), between an inner layer 46 of a comfortably soft yet strong fabric such as a Nylon tricot material, on the side of the main body 14 intended to be placed against a person, and an exterior layer 48 of a strong fabric such as a tricot material of Nylon or another synthetic material brushed to produce a nap of fiber loops that can act as a loop-bearing fastener material capable of being engaged matingly by a hook-bearing flexible fastener material such as that well known under the trademark Velcro. As used herein, the terms "loop-bearing fastener material" and "hook-bearing fastener material" will refer to fastener material that functions similarly to the Velcro™ combination of loop-pile fabric and "thistle-cloth" to stick removably together. Thus, for example, such loop-bearing fastener material is a first kind of flexible fastener material and such hook-bearing material is a second kind of flexible fastener material that can matingly engage the first kind of flexible fastener material.

A binding 49 may be provided around the exterior margin of the main body 14, and an adhesive may also be used to keep the inner and exterior layers 46 and 48 together with the central layer.

An exterior side 50 of the intermediate portion 38 of the strap 30 may be covered by a layer of a flexible loop-bearing fastener material 52, securely attached to the strap 30, as by being sewn to the webbing. Such loop-bearing fastener material 52 ideally may be present along the entire exterior side or face 50 of the strap 30, the side that is exposed in the same general direction as the exposed face of the exterior layer 48, from a point abutting the outer end portion 34 to the second end portion 26 of the main body 14, and may be present on the inner end 28 of the strap 30.

A piece of hook-bearing fastener material 54 may be securely attached to the exterior side 50 of the outer end portion 34 of the strap 30, as by being sewn to the webbing material forming the loop 36. Thus the area hook-bearing fastener material 54 may abut against the loop-bearing fastener material 52 on the exterior side 50 of the intermediate portion 38 of the strap 30.

At least one area 58 of hook-bearing fastener material is located on the second end portion of the main body 14. Advantageously, each area 58 may be a narrow, elongate piece of hook-bearing fastener material with a width 60 less than the width 42 of the strap 30, and a length 62, extending generally parallel with the longitudinal axis 32 of the main body portion 14. Such elongate areas 58 may be separated laterally from one another by a distance 64. For example, where the width 42 of the strap 30 is two inches, the width 60 of each area 58 may be about 0.75 inch, and the distance 64 between areas 58 may be about one inch. The length 62 may be as great as can be accommodated in the second end portion 26 and thus may be, for example, in the range of about 5 inches to about 7.3 inches, depending on the size of the pelvic sling 12. As will be understood in light of subsequent explanation, the foregoing dimensions are not critical, but the relationships of the width 60 and the distance 64 with the width 42 of the strap 30 can provide significant functional advantages.

Figure 2:
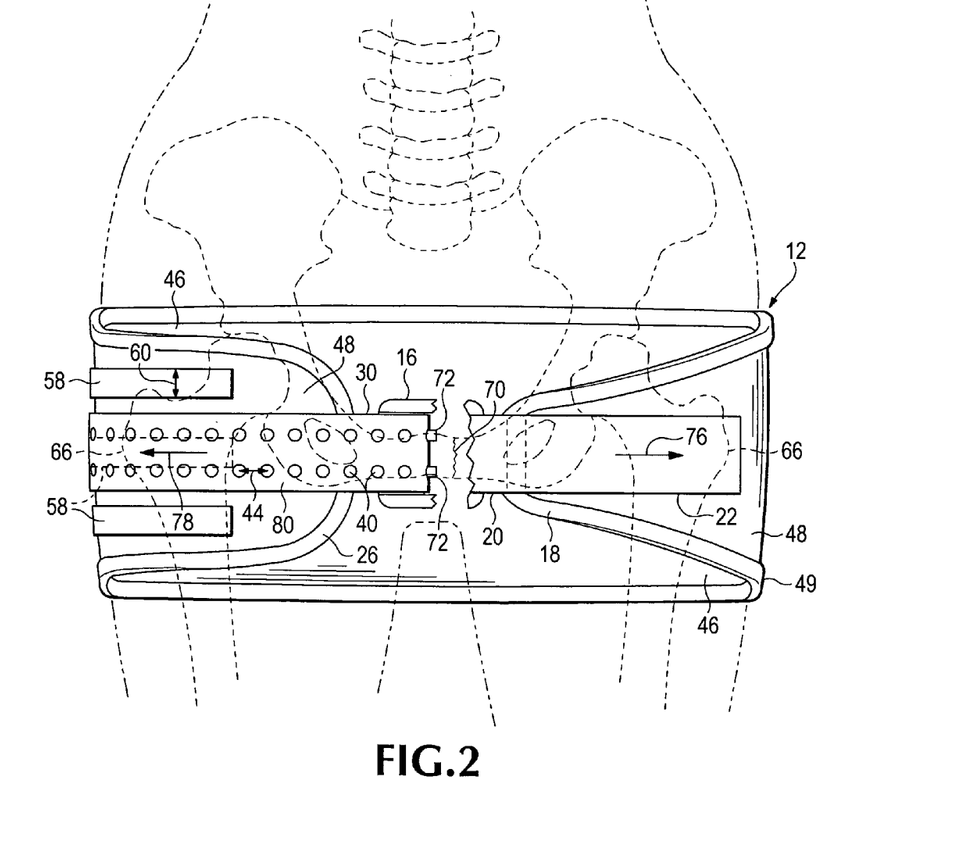
FIG. 2 is a front elevational partially cutaway view of the pelvis-stabilizing device shown in FIG. 1, showing the device extending around the pelvic area of a person and showing a portion of the skeleton of the person to illustrate the proper location of the device during use.

As may be seen in FIG. 2, when the pelvic sling 12 is properly in place on an injured person, it encircles the person's hips and buttocks at the level of the greater trochanters 66 and the symphysis pubis, with the main body portion 14 extending around the posterior of the person. The first and second ends 18 and 26 extend forward around the person's body and toward each other at the anterior side of the abdomen, with the strap 30 extending through the buckle 16 and doubled back toward the second end portion 26 of the main body portion 14, along the exterior of the pelvic sling 12. Although the pelvic sling 12 is shown consistently in one orientation herein, it is to be understood that it may be symmetrical in shape, about the central longitudinal axis 32, and thus can just as well be placed on a person with the buckle 16 and strap 30 oriented oppositely with respect to the person.

Figure 3:
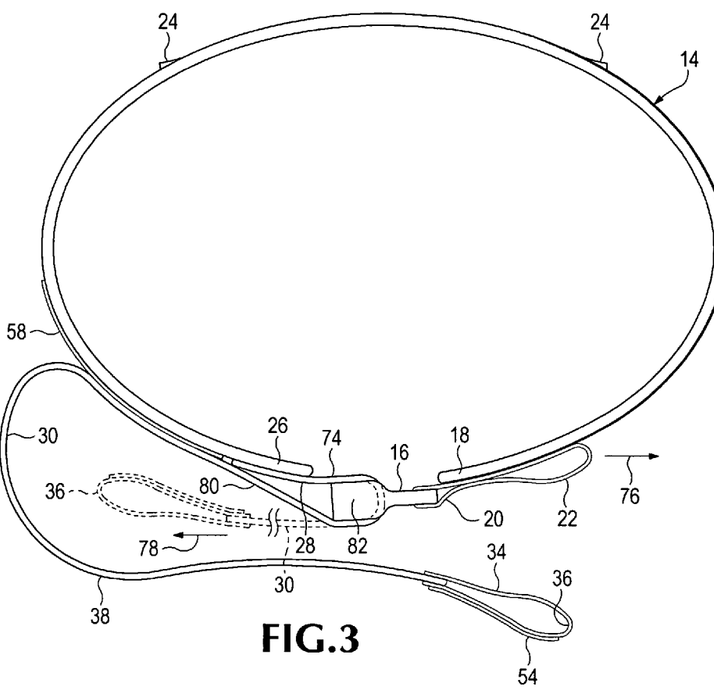
FIG. 3 is a top plan view of the pelvis-stabilizing device shown in FIGS. 1 and 2, under tension and with the strap shown secured so as to maintain tension to keep the buckle engaged while the device is fastened around a person of a minimum size for use of the device.
Figures 4, 5, 6:
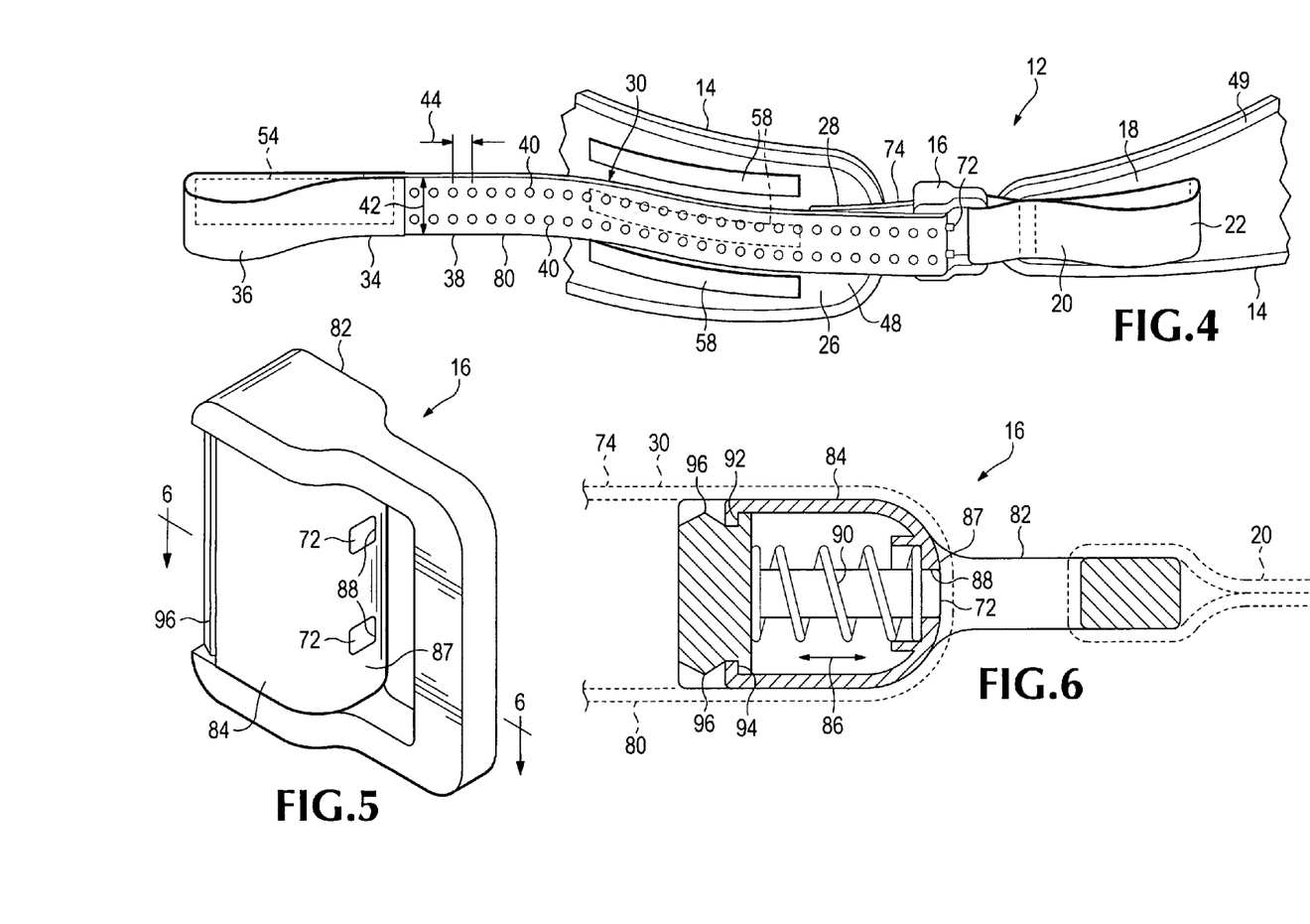
FIG. 4 is an isometric front view of end portions of the main body of the pelvis-stabilizing device shown in FIGS. 1-3, illustrating the device secured and under tension at a small circumference, as if to fit a slender person.
FIG. 5 is an isometric view of a buckle useful as a part of the pelvis-stabilizing device shown in FIGS. 1-4.
FIG. 6 is a sectional view of the buckle shown in FIG. 5, taken along line 6-6 of FIG. 5, with the buckle in a relaxed condition.

When the pelvic sling 12 is properly in place there is a prescribed amount of tension maintained in the main body portion 14 as it encircles the injured person, so that a fracture 70 in the pelvic ring is reduced. That is, the portions of the fractured bone are held together and stabilized by the tension in the pelvic sling 12. This tension is maintained by engagement of the buckle 16 with the strap 30. The desired amount of tension exerted on the buckle 16 by the strap 30 causes a portion of the buckle 16 to move, exposing pins 72 which extend through the ones of a pair of holes 40. As shown in FIGS. 2, 3, and 4, the outer, or pulled end, part 80 of the intermediate portion 38 of the strap 30 extends along the second end portion 26 of the main body 14, parallel with the outer surface of the exterior layer 48 when the device 12 is adjusted to a nearly minimum circumference. The loop-bearing fastener material 52 on the exterior side 50 of the strap 30 is aligned with and in mating contact with one of the areas 58 of hook-bearing fastener material, as shown in FIG. 2, so that the hook-bearing material 58 is matingly engaged with the loop-bearing fastener material 52 on the strap 30. Mating engagement of the fastener materials 58 and 52 is sufficient to maintain the tension in a portion 74 of the strap 30 between the inner end 28 and the buckle 16 to keep the pins 72 engaged in the holes 40 and thus keep the strap 30 engaged with the buckle 16.

Figure 7:
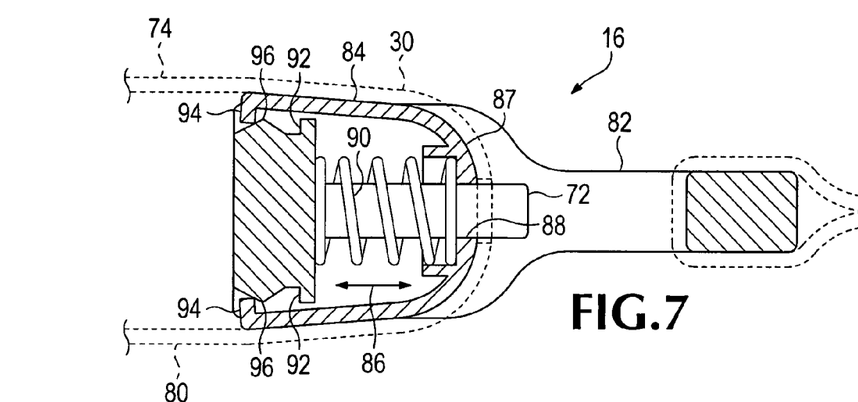
FIG. 7 is a view similar to FIG. 6, but showing the condition of the buckle when subjected to a predetermined tension to cause the buckle to engage a strap that is a part of the pelvis-stabilizing device shown in FIGS. 1-4.

The buckle 16 may be substantially similar to the buckle described in U.S. Pat. No. 7,008,389. Thus, as shown in FIGS. 5, 6, and 7, the buckle 16 includes two main parts, a rigid frame 82 and a sliding block 84. One side of the frame 82 is secured to the first end portion 18 of the main body portion 14 by a small loop of the fabric of the strap 20. The sliding block 84 is moveable relative to the buckle frame 82 in the directions indicated by the arrow 86. The strap 30 may extend through the opening defined by the frame 82, sliding along the contact surface of the curved face 87 of the sliding block 84 when the strap 30 is pulled to tighten the pelvic sling 12 about a person's pelvis. A pair of holes 88 are defined in the sliding block 84, and the pins 72 extend into the holes 88, with their ends preferably Rush with the face 87 when the buckle 16 is not in tension. When a pair of holes 40 in the strap 30 then move into alignment with the holes 88 in the sliding block 84 the sliding block 84 is moved leftward toward the position shown in FIG. 6, so that the pins 72 protrude from the holes 88 and can extend through the holes 40, thus engaging the strap 30 and preventing it from moving relative to the buckle 16, apart from any differences in size between the pins 72 and the holes 40.

FIGS. 6 and 7 show a spring 90 positioned around one of the pins 72. An identical spring 90 may be used on the other pin 72. The springs 90 are compressed significantly when the sliding block 84 is in its fully extended position, as shown in FIG. 5, so that substantial force must be applied to the buckle 16 by tension in the straps 20 and 30 before the sliding block 84 begins to move relative to the buckle frame 82. Internal springs 90 are compressed further as the sliding block 84 moves leftward toward the position shown in FIG. 6 when there is sufficient tension in the strap 30. Flanges 92 on the buckle frame 82 are engaged by lips 94 on the sliding block 84 when the sliding block 84 is in the fully extended position as shown in FIGS. 5 and 6, thus withstanding the compressive force in the springs 90.

As the sliding block 84 moves leftward toward the position shown in FIG. 2 from the position shown in FIG. 6, the lips 94 ride up and over the tops of the ramps 96 beneath the flanges 92, so that movement of the sliding block 84 may create an audible click as the sliding block 84 moves along the pins 72 and the pins extend into the holes 40, indicating to the user that the buckle 16 is engaged with the strap 30. Thereafter the inwardly directed elastic force in the sides of the sliding block 84 presses the lips 94 against the ramps 96 and helps to keep the pins 72 engaged in the holes 40, so that a slightly lower amount of tension in the portion 80 of the strap between the pins 72 and the loop 36 is sufficient to keep the sliding block in the leftwardly depressed position, once the pins 72 have become engaged in the holes 40 as shown in FIGS. 2 and 4.

As the strap 30, when the outer end 34 is pulled away from the buckle 16, passes over the curved face 87 of the sliding block, when the predetermined tension is applied to the buckle 16 by the strap 30, the sliding block 84 moves, further compressing the springs 90 and allowing the pins 72 to extend from the holes 88 and proceed through the holes 40, preventing further movement of the strap 30 around the sliding block 84. The holes 40 in the strap 30 may have a slightly larger diameter than the largest transverse dimension of the pins 72, so that engagement of the pins 72 in the holes 40 occurs easily and smoothly at the desired tension in the strap 30. Thus, as described in previously mentioned U.S. Pat. No. 7,008,389, when the proper amount of tension has been reached in the portion of the pelvic sling 12 wrapped around an injured person, the buckle 16 will engage the strap 30, and so long as tension in the pulled portion 80 of the strap 30 extending beyond the buckle 16 is not greatly reduced, the pins 72 will remain engaged in the holes 40. It will be understood that the buckle 16 could be constructed to include only one pin 72 or more than two pins 72 and that the strap 30 could be provided with compatibly located holes 40.

Once the pins 72 have engaged the holes 40, tension should be substantially maintained in the outer or pulled portion 80 of the strap 30, and the pulled portion 80 should be moved toward the person on whom the pelvic sling is being used and should be pressed against the outer end portion 26 of the main body 14 to engage the two mating kinds of fastener material with one another to retain the strap 30 at the desired location.

It would be possible to use other buckles (not shown), instead of the buckle 16, so long as such buckles can sense a predetermined amount of tension and engage the strap 30 in response.

As a result of the locations and sizes of the areas of hook-bearing fastener material 54 and 58 and the loop-bearing fastener material 52 on the exterior face 50 of the strap 30, the portion 80 of the strap 30 extending outside the buckle 16 and being pulled by a person applying the pelvic sling 12 to an injured person is able to be securely held by the combination of hook-bearing fastener material and loop-bearing fastener material at any effective circumference of the pelvis stabilizing pelvic sling device 12 at which the pins 72 of the buckle 16 may be engaged in a pair of holes 40 along the strap 30. Thus, as shown in FIGS. 2, 3, and 4, with the effective circumference of the pelvic sling 12 at or near a minimum, the area of hook-bearing fastener material 58 aligned centrally along the second end portion 26 of the main body is engaged with a confronting portion of the loop-bearing fastener material 52 on the exterior side 50 of the strap 30. An available area of hook and loop fastener engagement is thus equal to the area of the hook-bearing fastener material 58 of one of the 3 strips shown in FIG. 1, and the mated fastener materials can hold the outer, or pulled end, portion 80 of the strap 30 securely enough to maintain enough tension in that portion 80 of the strap 30 so that the pins 72 of the buckle remain exposed beyond the sliding block 84 and engaged in the holes 40 of the strap 30.

Figure 8:
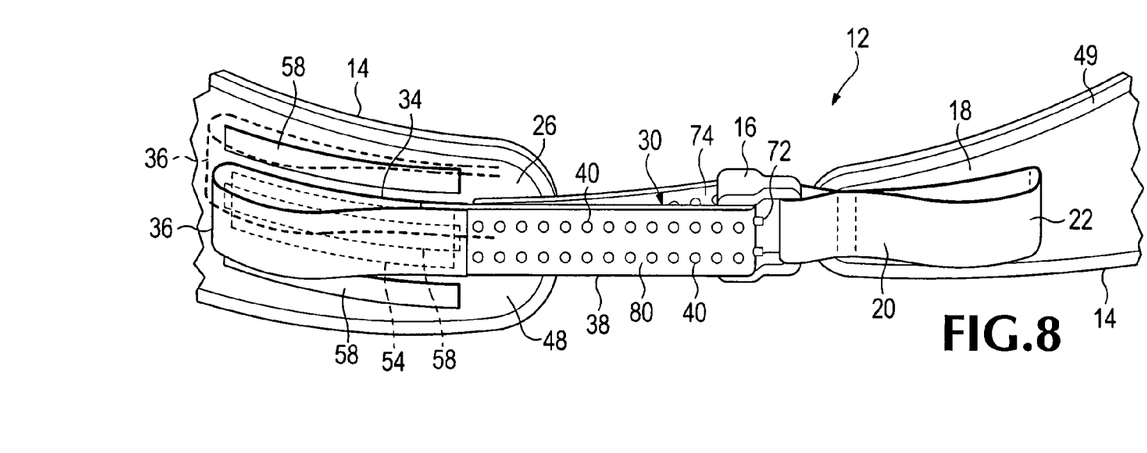
FIG. 8 is a view similar to FIG. 4 showing the pelvis-stabilizing and supporting device under tension so that the buckle engages the strap, at a larger circumference than that shown in FIG. 4, as if properly in place on a larger person.

In FIG. 8, the pelvis-stabilizing pelvic sling 12 is shown in tension as when in place on a person having a larger girth, and the loop-bearing fastener material 52 of the intermediate portion 38 of the strap 30 is not aligned with the area of hook-bearing fastener material 58. Instead, as shown in FIG. 8 the hook-bearing fastener material 54 mounted on the loop 36 of the outer end portion 34 is engaged with the loop-bearing fabric of the exterior layer 48 of the outer end portion 26 of the main body 14 on each side of the centrally located area of hook-bearing fastener material 58. As previously mentioned the fabric of the exterior layer 48 functions as loop-bearing fastener material. Accordingly, engagement of the area of hook-bearing fastener material 54 with the fabric 48 maintains sufficient tension in the outer, or pulled, portion 80 of the strap 30 to keep the pins 72 of the buckle 16 engaged in a pair of holes 40 in the strap 30, to maintain the proper amount of tension in the pelvic sling 12 to support and stabilize a person's fractured pelvis. It will be apparent that the loop 36 could be located slightly differently with the same position of the strap 30 with respect to the buckle, as shown in broken line. Thus the hook-bearing fastener material 54 could engage the fabric of the exterior layer 48 largely between two of the areas 58 of hook-bearing fastener material, overlapping somewhat on each of the areas 58, rather than by straddling a single area 58.

Figure 9:
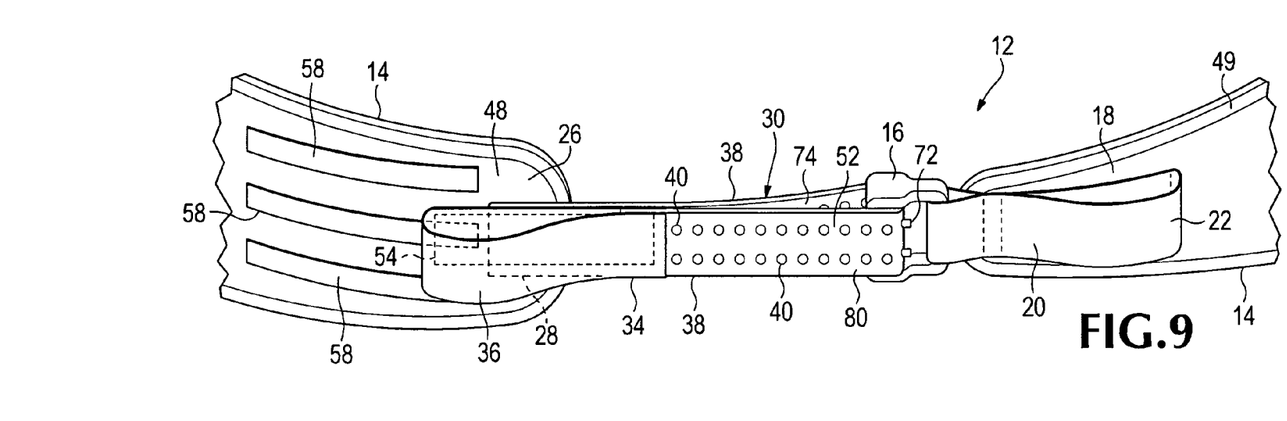
FIG. 9 is a view similar to FIG. 8, showing the pelvis-stabilizing and supporting device with the strap under tension and engaged by the belt at yet a larger circumference than that shown in FIG. 8, as if properly secured in place on a yet larger person.

As shown in FIG. 9, with the pelvis-stabilizing pelvic sling 12 in place under proper tension on a somewhat larger person than in FIG. 8, the hook-bearing fastener material 54 on the loop 36 at the outer end 34 of the strap 30 may be engaged with loop-bearing fastener material 52 at the inner end 28 of the strap 30 where it is attached to the second end portion 26 of the main body 14 and may also be engaged with the fiber loops of the fabric of the exterior layer 48 of the outer end portion 26, to the extent that the area of hook-bearing fastener material 54 extends beyond the inner end portion 28 of the strap 30.

Figure 10:
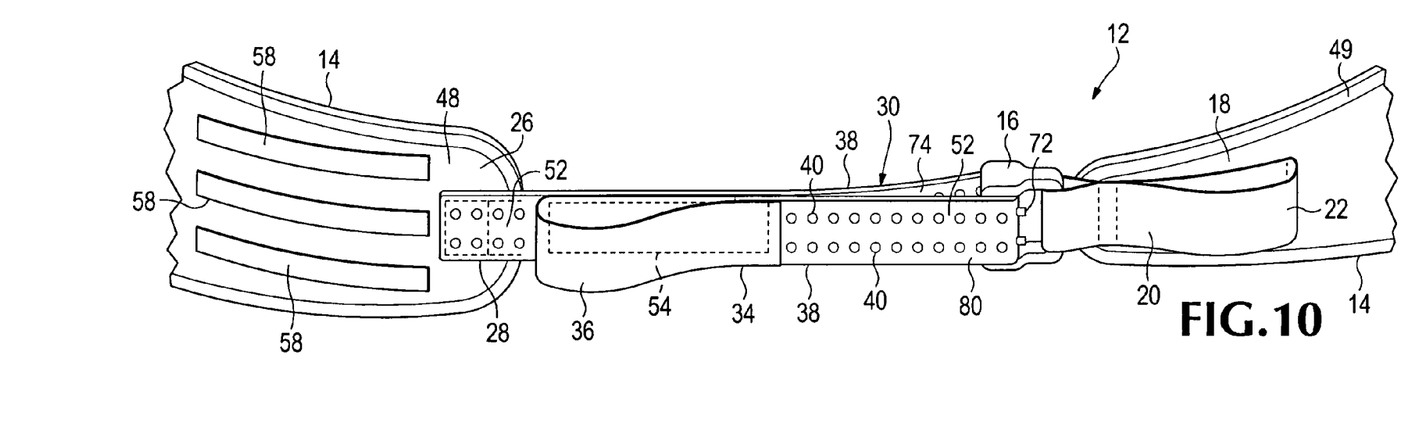
FIG. 10 is a view similar to FIG. 9, showing the pelvis-stabilizing and supporting device with the strap under tension and engaged by the buckle as if properly secured in place around a person of yet larger circumference, near the maximum for the size of the device.

As may be seen in FIG. 10, with the pelvis-stabilizing pelvic sling 12 under the proper amount of tension to stabilize and support a fractured pelvis in an even larger person, the hook-bearing fastener material 54 on the loop 36 at the outer end of the strap 30 can mate securely with the loop-bearing fastener material 52 on the portion 74 of the strap 30 between the second end portion 26 of the main body 14 and the buckle 16. The mated hook-bearing fastener material 54 and loop-bearing fastener material 52 securely maintain sufficient tension in the strap 30 as it is engaged with the buckle 16 to keep the pins 72 engaged in a pair of holes 40 in the strap 30.

Thus by referring to FIGS. 4, 8, 9, and 10, it may be seen that, regardless of the circumference of the person on whom the device 12 is being used, within a relatively wide range of different circumferences, application of the device 12 is very straightforward. As a result of the availability and locations of the areas of flexible fastener material of two mating kinds, located on the second end portion 26 of the main body 14, on the strap 30, and on the loop 36, the outer, or pulled, end, portion 80 of the strap 30 that extends beyond the buckle 16 can be fastened securely enough to maintain tension in the strap 30 to act against the sliding block 84 and thus maintain engagement of the buckle 16 with the pins 72 in any of the pairs of holes 40 along the part of the strap 30 extending beyond the second end portion 26 of the main body 14.

As the inner end portion 28 of the strap 30 is permanently attached to the second end portion 26 of the main body 14, adjustment of the pelvic sling 12 to provide the required amount of compression of the pelvis of an injured person is accomplished by pulling the strap 30 through the buckle 16, without first having to assemble any parts of the device. The pelvic sling 12 is placed around the hips of an injured person suspected of having a broken pelvis by sliding the main body portion 14 beneath the hips of the injured person. With the person lying in a supine position, the exterior side of the main body 14, the side shown in FIG. 1, should be downward. This permits the low friction plastic sheet 24 to slide easily along a surface of a backboard or other surface on which the person is resting, and exposes the necessary portions of the pelvic sling 12 so that it can be fastened.

Proper application of the pelvic sling 12 to an injured person thus can be accomplished simply and rapidly. First the sling should be placed at the level of the greater trochanters 66 and symphysis pubis, and the loop 36 and strap 30 must be passed through the opening in the frame 82 of the buckle 16 and around the curved face 87 of the sliding block 84. The pelvic sling can be tightened around a person by pulling the strap 30 and the buckle 16 in opposite directions, using the large loop 22 as a handle to pull toward the patient's left, as shown by the arrow 76, and, by using the large loop 36 as a handle, pulling the outer end 34 of the strap 30 in the opposite direction when the strap 30 extends through the buckle 16 and is doubled back toward the injured person's right side, as indicated by the arrow 78 in FIG. 2. The strap 30 is thus pulled through the buckle 16 until sufficient tension is achieved to move the sliding block 84 and allow the pins 72 to become engaged in a pair of holes 40 in the strap 30. While maintaining tension in the outer portion 80 of the strap 30 against the buckle 16, the flexible fastener materials can be engaged in one of the several alignments as described above to retain the tension in the strap 30 relative to the buckle 16 and thus to keep the pins 72 engaged in the holes 40 of the strap 30 at any effective circumference of the pelvic sling 12 at which the pins 72 are able to become engaged in a pair of holes 40.

Thus, engagement of the loop-bearing fastener material 52 of the strap 30 with the hook-bearing material in the areas 58 on the second end portion gives a first range of smallest available effective circumferences of the pelvic sling 12. Engagement of the fabric of the outer layer 48 of the second end portion of the main body 14 gives a second range of available, somewhat larger effective circumferences of the pelvic sling 12. Finally, engagement of the area 54 of hook-bearing fastener material of the outer end 34 of the strap with the (copy) loop-bearing fastener material 52 on the intermediate portion 38 of the strap 30 gives a third range of available effective circumferences, and the adjacent parts of the ranges overlap each other.

The pelvic sling 12 is made from a minimal number of components, and preferably of materials which are, except for the springs 90, radiolucent, and is ready for application as manufactured.

The pelvic sling 12 may be provided in various sizes. A normal size pelvic sling 12 may have a length of its main body length 98 of it main body of, for example, 24 inches, and larger and smaller sizes may be provided for use with very slender or very large persons. For a normal size pelvic sling 12 the length of the strap 30 combined with the extent of the loop 36 may be similar to or slightly shorter than the main body length 98.

While the description above has described the use of hook-bearing fastener material and loop-bearing fastener material, other two-component flexible fastener systems could also be used by similar placement of areas of the two matable fastener kinds on the strap 30 and a second end portion of a main body 14.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. A device for stabilizing a fractured pelvis, comprising:
   (a) an elongate main body portion having opposite first and second end portions;
   (b) a buckle fixedly attached to said first end portion of said main body portion;
   (c) a flexible elongate strap having an inner end permanently attached to said second end portion of said main body portion, the strap extending away from the main body portion and having an outer end portion opposite from said inner end thereof, the strap being of a size to pass through the buckle and the buckle being adapted to engage the strap so as to interconnect the first and second end portions of the main body portion with each other, and an intermediate portion of the strap, located between the outer end portion of the strap and the second end portion of the main body, having an area of flexible fastener material of a first kind located on a first side of the strap;
   (d) an area of flexible fastener material of a second kind that is cooperatively mateable with the flexible fastener material of the first kind, located on the outer end portion of the strap;
   (e) an area of flexible fastener material of the first kind located in the second end portion of the main body portion where the outer end portion of the strap can be fastened to the second end portion of the main body by mating cooperation of the respective areas of flexible fastener material of the first and second kinds, when the device is adjusted to a circumference in a predetermined first range of circumferences; and
   (f) an area of flexible fastener material of the second kind, located on the second end portion of the main body portion adjacent the area of flexible fastener material of the first kind, where the intermediate portion of the strap can be fastened to the second end portion of the main body portion by mating cooperation of the flexible fastener material of the first kind located on the intermediate potion of the strap with the flexible fastener material of the second kind located on the second end portion of the main body when the device is adjusted to a circumference in a range of circumferences smaller than said first range of circumferences.

2. The device of claim 1 wherein the area of said flexible fastener material of the first kind on the intermediate portion of the strap extends from the outer end portion of the strap to the second end portion of the main body portion.

3. The device of claim 1 wherein, when the strap extends through the buckle and is doubled back along itself toward the second end portion of the main body portion, the outer end portion of the strap can be fastened to a selected one of either the intermediate portion of the strap or the second end portion of the main body portion by mating engagement of the areas of fastener material of the first and second kinds, to hold the strap with the circumference of the device in a third range of effective circumferences.

4. The device of claim 1 wherein the first kind of flexible fastener material is a loop-bearing fastener material and the second kind of flexible fastener material is a hook-bearing material.

5. The device of claim 1 wherein the strap has a width and the second end portion of the main body portion has located thereon at least two of said areas of flexible fastener material of the second kind of elongate shape and extending parallel with each other and separated from each other by a distance less than the width of the strap.

6. The device of claim 5 wherein each of the areas of flexible fastener material of the second kind located on the second end portion has a width that is less than the width of the strap.

7. The device of claim 1 wherein the strap defines at least one hole and the buckle includes a base portion and a slide portion and has at least one pin projecting from the base portion, the slide portion having a contact surface and being mounted over the at least one pin and being movable relative to the base portion, and the slide portion being spring-biased toward a non-engaging position in which the at least one pin does not project beyond the contact surface of the slide portion, whereby the strap is free to slide freely over the contact surface until tension in the strap applies sufficient force to the slide portion to move the slide portion toward the base portion far enough for the at least one pin to project beyond the contact surface of the slide portion and engage said at least one hole in the strap, thereby establishing a position of the strap with respect to the buckle at a preselected tension level.

8. The device of claim 7 wherein the at least one hole includes a plurality of holes at respective spaced-apart locations in the strap between the outer end portion and the inner end of the strap.

9. The device of claim 1 wherein the second end portion of the main body portion has an outer layer of a flexible fabric having a nap of fiber loops capable of acting as a loop-bearing fastener material and mating securely with a confronting area of hook-bearing fastener material.

10. The device of claim 1 wherein the area of flexible fastener material of the second kind located on the outer end of the strap is located on the first side of the strap, so as to confront the area of flexible fastener material of the first kind on the intermediate portion of the strap when the strap is engaged with the buckle and doubled back along itself.

11. Apparatus for stabilizing a fractured pelvis, comprising:
   (a) a belt including a strap defining at least one hole;
   (b) a buckle including a base portion and having at least one pin projecting from the base portion, the at least one pin being dimensioned to fit in the at least one hole of the strap, and the buckle also including a slide portion, the slide portion having a contact surface, the slide portion being movable relative to the base portion and being mounted over the at least one pin and being spring-biased toward a non-engaging condition of the buckle in which the at least one pin does not project beyond the contact surface of the slide portion and the strap is to slide over the contact surface, and the slide being movable to an engaging condition of the buckle when tension in the strap applies sufficient force to the slide portion to move it toward the base portion far enough for the at least one pin to project beyond the contact surface of the slide portion and engage said at least one hole in the strap, thereby establishing a position of the strap with respect to the buckle at a preselected tension level, and wherein the belt includes a main body having a first end portion and an opposite second end portion, said buckle being attached to said first end portion of the main body and said strap extending from said second end portion of the main body;

(c) an inner end portion of said strap being attached to second end portion of said main body and an outer end portion of said strap being attached to said inner end portion and spaced apart from said second end portion, said strap having an outer face and including an area of said hook-bearing fastener material on said outer face of said outer end part of said strap, and said outer face of said inner portion of said strap including an area of loop-bearing fastener material; and (d) an area of loop-bearing fastener material and an adjacent area of hook-bearing fastener material being located on said second end portion of said main body, whereby the hook-bearing fastener material on the outer end portion of the strap can selectively be engaged matingly with the loop-bearing fastener material of said inner portion of said strap or with the loop-bearing fastener material on the second end of said main body when said strap is engaged by said buckle within a first range of circumferences of said belt, and whereby said loop-bearing fastener material of said inner portion of said strap can be engaged with said hook-bearing fastener material on said second end portion of said main body when said device is adjusted to a circumference within a second range of smaller circumferences.

12. A method of stabilizing and supporting a fractured pelvis of a person, comprising:

(a) applying a device having an elongate belt-like main body including opposite first and second end portions around the person in a position aligned with the pelvis;

(b) passing a strap permanently attached to and extending from the second end portion through a buckle attached to the first end portion and applying a predetermined amount of tension in the strap against the buckle, thereby urging the first and second end portions toward each other and compressing the pelvis with a predetermined amount of force;

(c) engaging the buckle to hold the strap and thereby retain the predetermined amount of tension; and (d) securing a portion of the strap that extends from the buckle so as to keep the buckle engaged, compressing the pelvis with a predetermined amount of compressive force, by:

(i) matingly engaging a flexible fastener material of a first kind carried on an outer end portion of the strap with a flexible fastener material of a second kind located on an the second end portion of the main body when the person has a circumference in a first range;

(ii) matingly engaging the flexible fastener material of the first kind located on the outer end portion of the strap with flexible fastener material of the second kind located on a intermediate portion of the strap when the person has a circumference in a second range; and (iii) matingly engaging the fastener material of the second kind located on the intermediate portion of the strap with fastener material of the first kind located on the second end portion of the main body when the person has a circumference in a third range.

\* \* \* \* \*

UNITED STATES PATENT AND TRADEMARK OFFICE
CERTIFICATE OF CORRECTION

| | | |
|---|---|---|
| PATENT NO. | : 8,192,383 B2 | Page 1 of 1 |
| APPLICATION NO. | : 12/462754 | |
| DATED | : June 5, 2012 | |
| INVENTOR(S) | : Adrian Abram Polliack and Lance David Hopman | |

It is certified that error appears in the above-identified patent and that said Letters Patent is hereby corrected as shown below:

Column 5, line 48: change "Rush" to --flush--.

Signed and Sealed this
Twenty-eighth Day of August, 2012

David J. Kappos
*Director of the United States Patent and Trademark Office*